(12) United States Patent
Howald et al.

(10) Patent No.: US 8,394,149 B2
(45) Date of Patent: Mar. 12, 2013

(54) METHOD FOR IMPLANTATION OF A FEMORAL IMPLANT

(75) Inventors: Ralph Howald, Gossau (CH); Peter Heuberger, Raterschen (CH); Daniel Hertig, Uhwiesen (CH); Job-Jan Greeve, BE Zutphen (NL)

(73) Assignee: Zimmer, GmbH, Winterthur (CH)

( * ) Notice: Subject to any disclaimer, the term of this patent is extended or adjusted under 35 U.S.C. 154(b) by 28 days.

(21) Appl. No.: 12/858,556

(22) Filed: Aug. 18, 2010

(65) Prior Publication Data

US 2010/0312353 A1    Dec. 9, 2010

Related U.S. Application Data

(62) Division of application No. 12/065,228, filed as application No. PCT/EP2006/065869 on Aug. 31, 2006, now Pat. No. 7,779,087.

(30) Foreign Application Priority Data

Aug. 31, 2005  (EP) ...................................... 05018940

(51) Int. Cl.
    *A61F 2/36*    (2006.01)
(52) U.S. Cl. ..................................... 623/23.12; 623/908
(58) Field of Classification Search ............... 623/22.12, 623/22.21, 22.44, 23.11–23.14, 23.42–23.43, 623/902, 908
    See application file for complete search history.

(56) References Cited

U.S. PATENT DOCUMENTS

| | | | |
|---|---|---|---|
| 1,448,111 A | | 3/1923 | Eppler |
| 2,718,228 A | * | 9/1955 | Steenbrugghe ............ 623/23.14 |
| 4,224,699 A | | 9/1980 | Weber |
| 4,312,079 A | | 1/1982 | Dorre et al. |
| 4,355,429 A | | 10/1982 | Mittelmeier et al. |
| 4,467,479 A | | 8/1984 | Brody |

(Continued)

FOREIGN PATENT DOCUMENTS

| | | |
|---|---|---|
| DE | 1164019 B1 | 2/1964 |
| DE | 2015324 A1 | 11/1971 |

(Continued)

OTHER PUBLICATIONS

Biomch-L, "Knee Arthropometry" Aug. 4, 1996, CGA FAQ, p. 2.

(Continued)

*Primary Examiner* — David Isabella
*Assistant Examiner* — Marcia Hoffman
(74) *Attorney, Agent, or Firm* — Schwegman, Lundberg & Woessner P.A.

(57) ABSTRACT

The invention relates to a cap-shaped implant for implanting on a prepared stump of a femoral head. The implant is in the form of a ball section, having a flat base surface and a polar axis which is arranged in a perpendicular in relation to the base surface. According to the invention, a cavity is arranged in ball section which protrudes from the base surface, said cavity is rotationally symmetrical and comprises a hollow spatial axis which is arranged below an angle (a) which is different form zero in relation to the polar axis.

10 Claims, 7 Drawing Sheets

U.S. PATENT DOCUMENTS

| | | | |
|---|---|---|---|
| 4,502,161 A | 3/1985 | Wall | |
| 4,532,661 A * | 8/1985 | Halpern | 623/23.14 |
| 4,769,039 A | 9/1988 | Horber | |
| 4,839,215 A | 6/1989 | Starling et al. | |
| 4,896,663 A | 1/1990 | Vandewalls | |
| 4,932,969 A | 6/1990 | Frey et al. | |
| 4,966,924 A | 10/1990 | Hyon et al. | |
| 4,976,740 A | 12/1990 | Kleiner | |
| 5,041,138 A | 8/1991 | Vacanti et al. | |
| 5,080,678 A | 1/1992 | Sportorno et al. | |
| 5,147,904 A | 9/1992 | Jocum et al. | |
| 5,217,498 A | 6/1993 | Henssge et al. | |
| 5,246,459 A | 9/1993 | Elias | |
| 5,271,737 A | 12/1993 | Baldwin et al. | |
| 5,282,861 A | 2/1994 | Kaplan | |
| 5,312,409 A | 5/1994 | McLaughlin et al. | |
| 5,314,478 A | 5/1994 | Oka et al. | |
| 5,358,525 A | 10/1994 | Fox et al. | |
| 5,370,700 A | 12/1994 | Sarkisian et al. | |
| 5,405,403 A | 4/1995 | Mikhail | |
| 5,458,643 A | 10/1995 | Oka et al. | |
| 5,553,476 A | 9/1996 | Oehy et al. | |
| 5,556,429 A | 9/1996 | Felt | |
| 5,607,474 A | 3/1997 | Athanasiou et al. | |
| 5,609,641 A | 3/1997 | Johnson et al. | |
| 5,645,592 A | 7/1997 | Nicolais et al. | |
| 5,658,343 A | 8/1997 | Hauselmann et al. | |
| 5,795,353 A | 8/1998 | Felt | |
| 5,817,098 A | 10/1998 | Albrektsson et al. | |
| 5,871,541 A | 2/1999 | Gerber | |
| 5,951,564 A | 9/1999 | Schroder et al. | |
| 6,132,468 A | 10/2000 | Mansmann | |
| 6,140,452 A | 10/2000 | Felt et al. | |
| 6,168,630 B1 | 1/2001 | Keller et al. | |
| 6,224,630 B1 | 5/2001 | Bao et al. | |
| 6,231,605 B1 | 5/2001 | Ku | |
| RE37,277 E | 7/2001 | Baldwin et al. | |
| 6,254,606 B1 * | 7/2001 | Carney et al. | 606/102 |
| 6,306,177 B1 | 10/2001 | Felt et al. | |
| 6,425,923 B1 | 7/2002 | Stalcup et al. | |
| 6,443,988 B2 | 9/2002 | Felt et al. | |
| 6,447,514 B1 | 9/2002 | Stalcup et al. | |
| 6,494,917 B1 | 12/2002 | McKellop et al. | |
| 6,530,956 B1 | 3/2003 | Mansmann | |
| 6,533,818 B1 | 3/2003 | Webster et al. | |
| 6,547,828 B2 | 4/2003 | Scott et al. | |
| 6,620,196 B1 | 9/2003 | Treiu | |
| 6,629,997 B2 | 10/2003 | Mansmann | |
| 6,652,587 B2 | 11/2003 | Felt et al. | |
| 6,652,588 B2 | 11/2003 | Hays, Jr. et al. | |
| 6,679,913 B2 | 1/2004 | Homsy | |
| 6,719,797 B1 | 4/2004 | Ferree | |
| 6,827,743 B2 | 12/2004 | Eisermann | |
| 6,994,730 B2 | 2/2006 | Posner | |
| 7,001,431 B2 | 2/2006 | Bao et al. | |
| 7,077,865 B2 | 7/2006 | Bao et al. | |
| 7,291,169 B2 | 11/2007 | Hodorek | |
| 7,517,364 B2 * | 4/2009 | Long et al. | 623/19.14 |
| 2001/0012967 A1 * | 8/2001 | Mosseri | 623/23.12 |
| 2001/0033857 A1 | 10/2001 | Vyakaman et al. | |
| 2001/0039455 A1 | 11/2001 | Simon et al. | |
| 2002/0022884 A1 | 2/2002 | Mansmann | |
| 2002/0029083 A1 | 3/2002 | Zucherman et al. | |
| 2002/0127264 A1 | 9/2002 | Felt et al. | |
| 2002/0156531 A1 | 10/2002 | Felt et al. | |
| 2002/0161448 A1 | 10/2002 | Hayes, Jr. et al. | |
| 2002/0173852 A1 | 11/2002 | Felt et al. | |
| 2002/0173855 A1 | 11/2002 | Mansmann | |
| 2002/0183845 A1 | 12/2002 | Mansmann | |
| 2002/0183850 A1 | 12/2002 | Felt et al. | |
| 2002/0188300 A1 | 12/2002 | Arramon et al. | |
| 2002/0193883 A1 | 12/2002 | Wironen | |
| 2003/0008396 A1 | 1/2003 | Ku | |
| 2003/0074076 A1 | 4/2003 | Ferree et al. | |
| 2003/0078617 A1 | 4/2003 | Schwartz et al. | |
| 2003/0130741 A1 | 7/2003 | McMinn | |
| 2003/0153918 A1 | 8/2003 | Putnam et al. | |
| 2003/0163202 A1 | 8/2003 | Lakin | |
| 2003/0195628 A1 | 10/2003 | Bao et al. | |
| 2003/0220649 A1 | 11/2003 | Bao et al. | |
| 2004/0010312 A1 | 1/2004 | Enayati | |
| 2004/0039447 A1 | 2/2004 | Simon et al. | |
| 2004/0051213 A1 | 3/2004 | Muratoglu | |
| 2004/0107000 A1 | 6/2004 | Felt et al. | |
| 2004/0133275 A1 | 7/2004 | Mansmann | |
| 2004/0138754 A1 | 7/2004 | Lang et al. | |
| 2004/0153163 A1 | 8/2004 | Posner | |
| 2004/0163681 A1 | 8/2004 | Verhaverbeke | |
| 2004/0199250 A1 | 10/2004 | Fell | |
| 2004/0220582 A1 | 11/2004 | Keller | |
| 2004/0236424 A1 | 11/2004 | Berez et al. | |
| 2004/0247641 A1 | 12/2004 | Felt et al. | |
| 2004/0267371 A1 | 12/2004 | Hayes, Jr. et al. | |
| 2005/0021042 A1 | 1/2005 | Marnay et al. | |
| 2005/0043808 A1 | 2/2005 | Felt et al. | |
| 2005/0075642 A1 | 4/2005 | Felt et al. | |
| 2005/0125077 A1 | 6/2005 | Harmon et al. | |
| 2005/0171604 A1 | 8/2005 | Michalow | |
| 2005/0251149 A1 | 11/2005 | Wenz | |
| 2005/0251266 A1 | 11/2005 | Maspero et al. | |
| 2005/0287187 A1 | 12/2005 | Mansmann | |
| 2006/0009853 A1 | 1/2006 | Justin et al. | |
| 2006/0079905 A1 | 4/2006 | Beyar et al. | |
| 2006/0224244 A1 | 10/2006 | Thomas et al. | |
| 2006/0235542 A1 | 10/2006 | Hodorek et al. | |
| 2006/0253200 A1 | 11/2006 | Bae et al. | |
| 2007/0027230 A1 | 2/2007 | Beyar et al. | |
| 2007/0038300 A1 | 2/2007 | Bao et al. | |
| 2007/0088444 A1 | 4/2007 | Hodorek | |
| 2007/0142916 A1 | 6/2007 | Olson et al. | |
| 2007/0149979 A1 * | 6/2007 | Chana | 606/96 |
| 2007/0179607 A1 | 8/2007 | Hodorek et al. | |
| 2007/0224238 A1 | 9/2007 | Mansmann et al. | |
| 2008/0051889 A1 | 2/2008 | Hodorek | |
| 2008/0215057 A1 | 9/2008 | Willi | |
| 2008/0221700 A1 | 9/2008 | Howald | |

FOREIGN PATENT DOCUMENTS

| | | |
|---|---|---|
| DE | 2501080 A1 | 7/1976 |
| DE | 2933174 A1 | 4/1980 |
| DE | 2953575 A1 | 7/1982 |
| DE | 3923418 A1 | 1/1991 |
| DE | 4317448 A1 | 11/1994 |
| DE | 29513894 U1 | 10/1995 |
| DE | 19721661 A1 | 11/1998 |
| DE | 19803183 A1 | 8/1999 |
| DE | 10021387 A1 | 11/2001 |
| DE | 20303205 U1 | 4/2003 |
| DE | 10220368 A1 | 12/2003 |
| DE | 10339605 A1 | 4/2005 |
| EP | 0013863 A1 | 8/1980 |
| EP | 0013864 A1 | 8/1980 |
| EP | 0017930 A1 | 10/1980 |
| EP | 0170779 A1 | 2/1986 |
| EP | 0480954 B1 | 4/1992 |
| EP | 0528080 A1 | 2/1993 |
| EP | 0552949 A1 | 7/1993 |
| EP | 0577529 A1 | 1/1994 |
| EP | 0639356 A1 | 2/1995 |
| EP | 0768066 A2 | 4/1997 |
| EP | 0892627 B1 | 1/1999 |
| EP | 0992222 A2 | 4/2000 |
| EP | 0507645 B1 | 7/2001 |
| EP | 1340477 A2 | 9/2003 |
| EP | 1407728 A1 | 4/2004 |
| EP | 1477120 A1 | 11/2004 |
| EP | 1588669 A1 | 10/2005 |
| FR | 2519545 A1 | 7/1983 |
| FR | 2691355 A1 | 11/1993 |
| FR | 2692140 A1 | 12/1993 |
| FR | 2803190 A1 | 7/2001 |
| FR | 2803191 A1 | 7/2001 |
| GB | 1126961 A | 11/1968 |
| GB | 1349987 A | 4/1974 |
| GB | 2139097 A | 11/1984 |
| WO | WO97/37613 A1 | 10/1997 |
| WO | WO00/15153 A1 | 3/2000 |

| | | |
|---|---|---|
| WO | WO00/23009 A1 | 4/2000 |
| WO | WO01/45595 A2 | 6/2001 |
| WO | WO02/41808 A1 | 5/2002 |
| WO | WO02/054992 A1 | 7/2002 |
| WO | WO04/032987 A1 | 4/2004 |
| WO | WO2005/051242 A1 | 6/2005 |
| WO | WO2006/060555 A1 | 6/2006 |
| WO | WO2007/054553 A1 | 5/2007 |
| WO | WO2007/090790 A2 | 8/2007 |
| WO | WO2007/125060 A1 | 11/2007 |

OTHER PUBLICATIONS

Quinton, J.S. and P.C. Dastoor, "Characterizing the bonding mechanisms at silane-metal interfaces: a model system", J. Mat. Sci. Letters, vol. 18, Nov. 1999, pp. 1833-1835.

* cited by examiner a)

b)

a)

b)

METHOD FOR IMPLANTATION OF A FEMORAL IMPLANT

CROSS-REFERENCE TO RELATED APPLICATIONS

This is a Divisional of U.S. application Ser. No. 12/065,228 filed Feb. 28, 2008, which is a U.S. National Phase Patent Application based on International Patent Application Serial No. PCT/EP2006/065869 filed on Aug. 31, 2006, the disclosures of which are expressly incorporated by reference herein.

BACKGROUND

The present invention relates to an implant made in cap shape for implantation onto a prepared stump.

On the use of an implant made in cap shape of this type, the natural femoral head of the patent can largely be maintained. The femoral head is only worked on its surface in the operation in order to permit the placing on of the implant made in cap shape. This surgical procedure is also known as "resurfacing".

A resurfacing implant for a femoral head has become known from EP 1407728 that is provided with a spigot extending into the femoral neck for the anchorage. US 2003/0163202 discloses an implant that has a conical inner contact surface for fastening to a femoral head prepared in the form of a conical stump.

SUMMARY

Here, an implant made in cap shape of the initially named kind is now proposed that, in addition to a plurality of other advantageous properties, copies the articulation surface of the natural femoral head in a good manner, can be implanted with a low loss of bone material and ensures a good primary anchorage as well as a secure and reliable seat over a long time both with cemented and uncemented implantation. More specifically, it should, for example, be made possible to copy the geometry of the natural articulation surface, which is substantially symmetrical to the neck axis of the femoral head, by an artificial articulation surface formed by the outside surface of the femoral cap and simultaneously to ensure a secure fastening of the implant on the femoral head. It must be noted in this context that the main direction of application of the force introduced into the femoral head approximately follows a line directed from the femoral head to the distal end of the femur or even deviates even more pronouncedly from the axis of the neck of the femur. In accordance with a further aspect, the implant should be set forth such that it can be anchored securely on the prepared stump of a femoral head. A method should furthermore be set forth for the implantation of an implant made in cap shape. A method should also be set forth for the manufacture of the described implant made in cap shape. An instrument should furthermore be set forth for the manufacture of an implant made in cap shape.

In addition to other advantageous properties, the subjects described in the claims can also satisfy these demands. Properties such as the simple handling by the surgeon, the implanting capability with minimal incisions, or a with a minimal bone tissue loss, and an implantation gentle on soft parts are set as self-explanatory and are considered as to be satisfied.

The implant set forth has the shape of a spherical section with a planar base surface and a polar axis arranged perpendicular to the base surface. A rotationally symmetrical hollow space is arranged in the spherical section and starts from the base surface, that is has an opening which is disposed at least in part in the base surface. The hollow space has a hollow space axis which is arranged at an angle to the polar axis different than zero. This makes it possible for the implant to be able to be set onto the prepared stump such that the polar axis of the implant coincides with the neck axis of the femoral head. At the same time, the fastening of the implant can be carried out such that the hollow space axis of the hollow space of the implant coincides at least approximately with the main strain direction of the femoral head.

The hollow space axis in one embodiment intersects the polar axis, in particular at a spherical center of the spherical section. The polar axis and the hollow space axis include an angle with one another, for example, in the range from 15° to 50°, in particular from 15° to 35°. This, for example, covers the range in which the angle of inclination of the main strain direction is inclined against the axis of the neck. The spherical section, for example, has a spherical diameter in the range from 38 mm to 60 mm and a height measured from the base surface up to the pole in the direction of the polar axis of 60% to 80% of the spherical diameter. Said diameter range is typical for prostheses in which the femoral neck is maintained to ensure movability, and is selected, for example, in the range of the diameter of the natural femoral head. With these diameters, femur components made of metal are, for example, used such as have also been described in EP 892627 and, for example, also in combination with a metallic mating running surface, which has likewise become known from EP 892627; with these specifications representing an integral component of the present description. The cap height measured across the polar axis ensures a sufficiently large angular range in which the femoral cap makes available an effective articulation surface.

In an embodiment of the implant, the hollow space has an inner surface that has a penetration with the surface of the spherical section, with at least one peripheral segment of the inner surface having a penetration with a spherical surface region of the spherical section. In particular a first peripheral segment of the inner surface can penetrate the spherical surface region of the spherical section and a second peripheral segment of the inner surface can penetrate the base surface. The implant can therefore have a cap opening which is bounded by a margin of the implant, said margin only being arranged regionally in the plane of the base surface, i.e. not over the full periphery. A first region of the margin can be arranged in the plane of the base surface and a second region of the margin can be arranged in an entry plane oriented perpendicular to the hollow space axis. This means that the opening of the implant is then not planar, but is divided into two part surfaces which are each arranged perpendicular to the polar axis and perpendicular to the hollow space axis.

In a further embodiment, the hollow space has the shape of a conical stump which tapers along the hollow space axis in a direction facing the interior of the implant. Due to the conical stub shape, the stimulation of the bone tissue at the prepared stub can be increased to counter a degrading of bone material respectively to stimulate the ongrowth of bone material on the implant in that the cone is designed such that compression strain is present in all regions of the interface between the stump and the implant inner surface. Furthermore, conical surfaces can be manufactured simply. The conical stump has a full conical opening angle of, for example, 10° to 65°, in particular 16° to 50°.

In an embodiment of the implant, anchorage means are arranged in the interior of the hollow space for the anchorage of the implant on the stump, the anchorage means being arranged on the inner surface of the implant bounding the hollow space. They serve, for example, for a further improved primary anchorage of the implant on the bone and can also be used as security against the rotation of the implant on the bone stump, whereas an embodiment without anchorage means permits a less invasive implanting with a lower loss of bone material. Generally, the implant described is provided for cement-free implantation, with, however, an implantation using bone cement naturally generally also being possible. The anchorage means are arranged distributed symmetrically around the hollow space axis in an embodiment. In an arrangement of the anchorage means at the margin of the hollow space, the bone tissue in the center of the prepared stump of the femoral head remains undamaged. In an exemplary embodiment of the implant, the anchorage means comprise barb-like structures which are arranged at the periphery of the hollow space and are bent facing away from an opening of the hollow space into the interior of the implant. The bark-like structures are formed, for example, by a plurality of anchorage teeth whose height lies in the range from tenths of a millimeter to millimeters, for example around 1 mm, for example in the region from 0.5 mm to 1.5 mm. These structures are, for example, arranged concentrically around the hollow space axis. In a further embodiment of the implant, the anchorage means comprise a plurality of anchorage ribs, anchorage fins and/or anchorage pins oriented parallel to the hollow space axis and in particular serving the primary anchorage. In the case of anchorage fins, corresponding cut-outs can be manufactured in a simple manner in the fins by sawing or cutting into the femoral head using a corresponding saw blade. A weighing-up can be made between a loss of bone material, on the one hand, and the best possible anchorage on the other hand, with respect to the number of the individual anchorage elements.

To promote an ingrowth of bone material into the implant, the hollow space can be bounded by an inner surface which is rough blasted at least regionally and/or has a microstructure. An inner surface of the implant surrounding the hollow space has, for example, a titanium plasma coating. The inner surface can also be provided with a porous structure whose surface is surrounded by metal, in particular tantalum. Such a surface has, for example, become known under the trade name "Trabecular Metal" of the implant manufacturer ZIMMER.

The different aforesaid embodiments of an implant in accordance with claim 1 and the features realized there can naturally be combined with one another.

With the method set forth for the implanting of an implant, an implant made in cap shape is selected which comprises a hollow space with a hollow space axis. The femoral head is resected in such a manner as to obtain a prepared stump which represents a mating shape to the hollow space of the implant and is rotationally symmetrical with respect to an implantation axis, and indeed such that the implantation axis is inclined with respect to the femoral neck axis at least in a frontal plane, at most also, as described below, additionally in a sagittal plane. The inclination in the frontal plane lies, for example, in the range from 15° to 50°, in particular 15° to 35°, and is generally dimensioned such that the implantation axis coincides with the direction of the main strain of the femoral head. An implant can in particular be selected which is an implant of the type described above.

In an embodiment of the method for the implantation of the implant, a first drill wire is inserted into the femoral head along the femoral neck axis, an alignment instrument is placed onto the first drill wire, a second drill wire is inserted into the femoral head along the implantation axis inclined with respect to the femoral neck axis and the alignment instrument and the first drill wire are removed before the resecting of the femoral head, with the aforesaid steps in particular being carried out in this order. Instruments and methods with whose help the first drill wire can be centered on the femoral head and/or can be brought into alignment with the neck of the femur are known, such as, for example, the centering instrument for the implantation of the DUROM hip cap from ZIMMER. The alignment instrument includes an indication or guide means which serves to define the inclination of the implantation axis with respect to the neck axis and thus to define the implantation axis.

Alternatively, using suitable auxiliary means and/or methods, the second drill wire can also be implanted directly, without the aid of a first drill wire. The second drill wire is, for example, used as a guide tool in the working of the femoral head and/or is removed before placing the implant made in cap shape onto the prepared stump.

In an embodiment, the method for the implantation of an implant, in particular of an implant of the type described above, comprises implanting the implant such that the hollow space axis and the implantation axis coincide on the placing of the implant made in cap shape onto the prepared stump. The method for the implantation of the implant can additionally provide for the securing of the implant against tilting of the hollow space axis with respect to the implantation axis. The securing can consist of a guide for the implant, said guide being aligned in the direction of the implantation axis. An embodiment comprises working the femoral head such that the inclination of the implantation axis with respect to the femoral neck axis corresponds to the angle between the polar axis and the hollow space axis of the implant. Furthermore, in an embodiment, the implant is placed on such that the polar axis of the implant and the femoral neck axis coincide. A further exemplary embodiment of the method for the implantation of an implant comprises working the femoral head so that the implantation axis is inclined with respect to the femoral neck axis both in the frontal plane and in a sagittal plane, that is has a so-called antetorsion.

The different embodiments set forth above of an implantation method in accordance with the independent claim directed to an implantation method or the features realized there can naturally be combined with one another.

In the method set forth for the manufacture of an implant made in cap shape for a prepared stump of a femoral head, in particular of the aforesaid implant, a spherical section is manufactured having a planar base surface and a polar axis arranged perpendicular to the base surface and a rotationally symmetrical hollow space is generated having a hollow space axis in the fully spherical section, starting from the base surface, such that the hollow space axis is arranged at an angle different than zero to the polar axis. In this connection, for example, the spherical section having the planar base surface can be manufactured first and the hollow space can be introduced thereafter or the hollow space is first established in a sphere or in a spherical section and a planar surface is manufactured by a suitable method and is arranged perpendicular to a polar axis which includes an angle different than zero with the hollow space axis.

In the further method set forth for the manufacture of an implant made in cap shape, in particular of the aforesaid implant, for a prepared stump of a femoral head, grooves are generated at the inner surface of the hollow space, for example by means of a turning process, in order to obtain elevated portions at the inner surface in the form of concentric rings which are arranged concentrically around the hollow space axis. Finally, the ring-shaped elevated portions are notched by means of a stamping process to generate a plurality of anchorage teeth in each case from the concentric rings.

In this connection, the hollow space is generated in its manufacture with a diameter undersize with respect to the desired end dimension of the hollow space. In an embodiment of this method, the notches are generated while applying a force which is directed into the hollow space in the direction of the hollow space axis. The remaining elevated portions in corner regions which are arranged adjacent to the notches are thereby plastically deformed such that they face into the hollow space. A barb structure is thereby created for the anchorage of the implant. An instrument for the generation of the notches, in particular a stamping instrument, can in particular be introduced into the hollow space in the direction of the hollow space axis and be pressed against the elevated portions while applying a force directed into the hollow space in the direction of the hollow space axis to generate the notches. An instrument for the carrying out of such a method comprises a shaft part and a head part. The instrument can be gripped at the shaft part. The head part connected to the shaft part has at least two stamping edges for the generation of the notches. The stamping edges have contours in a side view which are a mating shape to the inner surface of the hollow space in a section of the implant parallel to the hollow space axis.

The method described for the manufacture of anchorage elements in the interior of implants is naturally not restricted to the cap-shaped element, but can be used in other implants which have an inner space which is designed for the contact to bones and at which a primary anchorage and an ingrowth should take place.

The working of the spherical articulation surface of the implant takes place, for example, using a method described in EP 1 340 477, the entire disclosure of which is hereby incorporated by reference herein.

A method for the implantation of an implant comprises choosing an implant made in cap shape which comprises a hollow space having a hollow space axis; resecting the femoral head so as to obtain a prepared stump representing a mating shape to the hollow space of the implant and being rotationally symmetrical with respect to an implantation axis; and working the femoral head so that the implantation axis is inclined at least in a frontal plane with respect to the femoral neck axis.

A further method further comprises inserting a first drill wire into the femoral head along the femoral neck axis; placing an alignment instrument onto the first drill wire, said alignment instrument comprising an indication or gauge means for defining the inclination of the implantation axis with respect to the femoral neck axis and thus defining the implantation axis; inserting a second drill wire into the femoral head along the axis inclined with respect to the femoral neck axis; and removing the alignment instrument and the first drill wire, all before the resecting of the femoral head.

In this context, in an embodiment of the method, a suitable auxiliary means, for example a mechanical auxiliary means, is used to localize the center of the femoral head in order to set on the alignment instrument such that the center of the rotation between the neck axis and the implantation axis coincides at least substantially with the center of the femoral head.

A further method further comprises using the second drill wire as a tool guide in resecting the femoral head.

A further method further comprises removing the second drill wire before placing the implant made in cap shape onto the prepared stump.

A further method further comprises implanting the implant such that the hollow space axis and the implantation axis coincide on the placing of the implant made in cap shape onto the prepared stump.

A further method further comprises securing the implant against tilting of the hollow space axis with respect to the inclined axis.

A further method further comprises choosing an implant that is an implant according to at least one of the claims 1 to 15.

A further method further comprises working the femoral head such that the inclination of the implantation axis with respect to the femoral neck axis corresponds to the angle between the polar axis and the hollow space axis of the implant.

A further method further comprises placing the implant such that the polar axis of the implant and the femoral neck axis coincide A further method further comprises working the femoral head so that the implantation axis is inclined with respect to the femoral neck axis both in the frontal plane and in a sagittal plane.

The invention will be explained in more detail in the following with reference to embodiments illustrated in the drawing. In this context, the embodiments and the drawing should only be understood in an instructive manner and should not serve for the restriction of the subjects described in the claims. The illustrations in the drawing are simplified; details not necessary for the understanding of the invention have been omitted.

BRIEF DESCRIPTION OF THE DRAWINGS

FIG. 3 shows the proximal part of a femur with an implant placed on.

Corresponding reference characters indicate corresponding parts throughout the several views. The exemplifications set out herein illustrate preferred embodiments of the invention, and such exemplifications are not to be construed as limiting the scope of the invention in any manner.

DETAILED DESCRIPTION

Figure 1A:
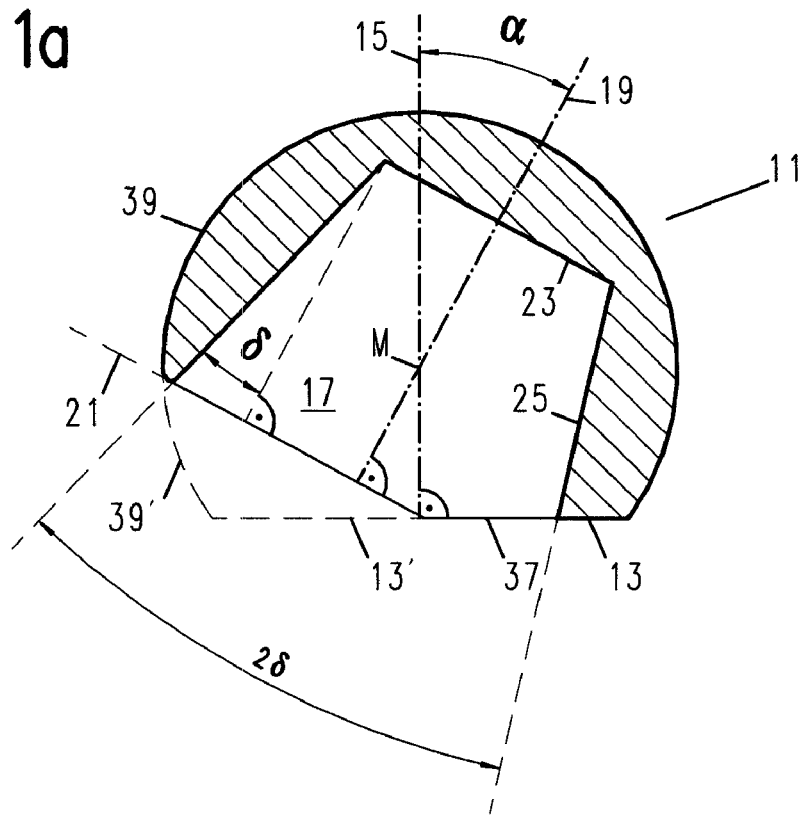
FIG. 1 shows two embodiments of an implant.
Figure 1B:
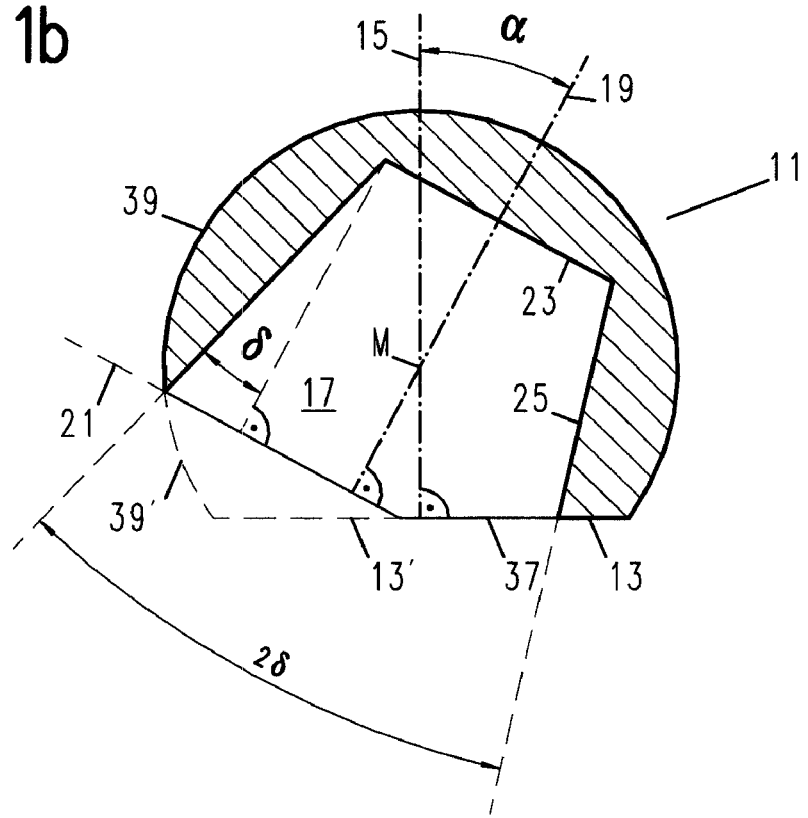
Figure 2:
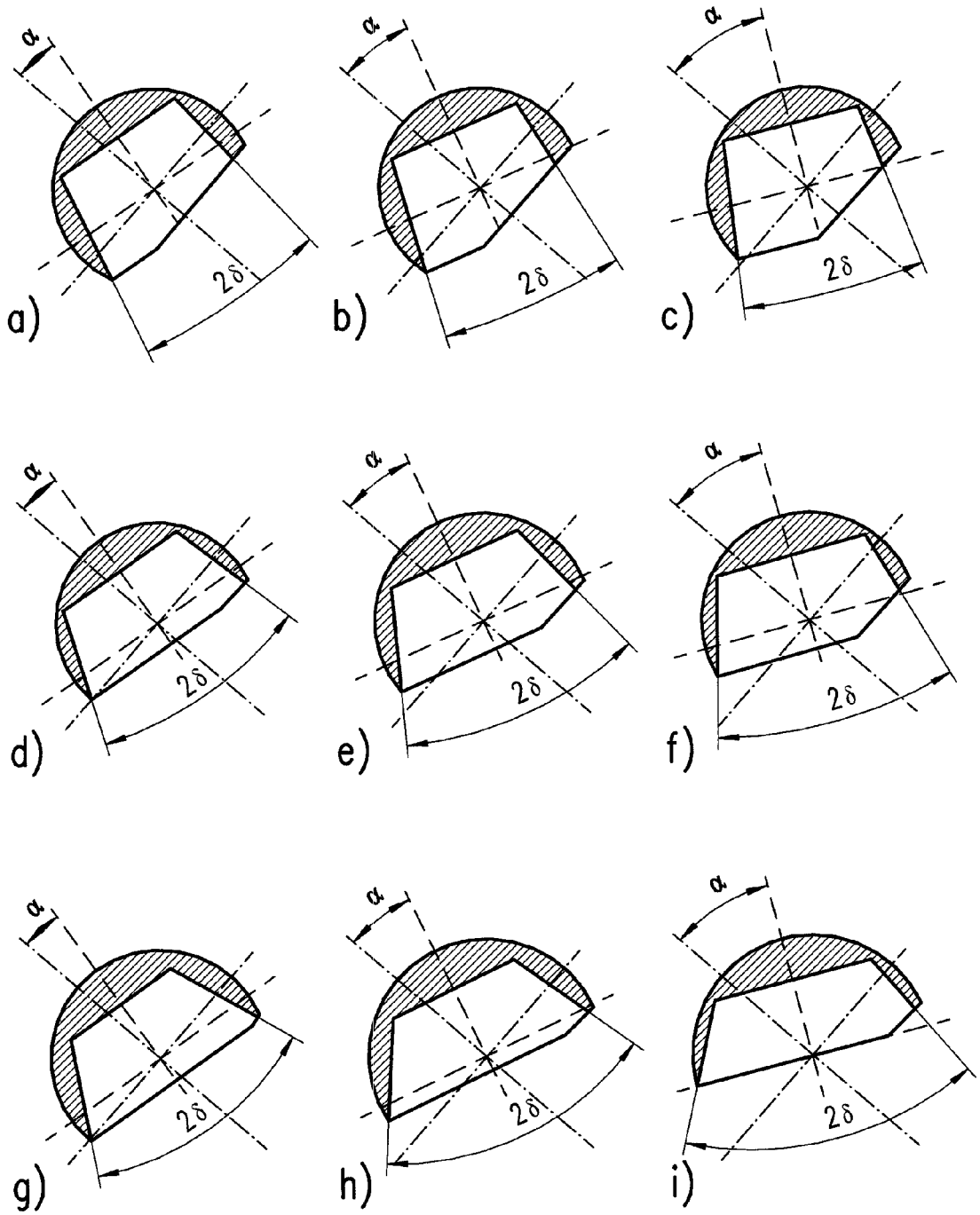
FIG. 2 shows further embodiments of an implant.

FIGS. 1a and 1b each show an embodiment of an implant made in the shape of a cap for implantation onto a prepared stump not shown in FIGS. 1a and 1b. The implant has the form of a spherical section 11 with a spherical center M, a spherical surface region 39 and a planar base surface 13, with a polar axis 15 being arranged perpendicular to the base surface 13. In addition, the spherical section 11 has a hollow space 17 which is made rotationally symmetrically around a hollow space axis 19. A spherical section with a spherical surface region 39' and a base surface 13' is indicated in a broken-line representation, said spherical section not having a hollow space, i.e. said spherical section not being superimposed with a hollow space. The hollow space 17 has the shape of a conical stump which tapers along the hollow space axis 19 in a direction facing into the interior of the implant. The hollow space 17 is bounded by an inner surface 23, 25 which comprises an end face 23 and a conical jacket surface 25 having a conical opening angle 28 or half a conical opening angle 8. The hollow space axis 19 and the polar axis 15 include an angle α different than zero and intersect at the center M of the spherical section 11. The jacket surface 25 of the hollow space 17 of the implant shown in FIG. 1 passes through both a part of the spherical surface region 39 and a part of the planar base surface 13. The hollow space 17 thus has a cap opening which is bounded by a margin 37, with at least one first part of the margin 37 being formed by the penetration of the jacket surface 25 having the spherical surface region 39 and being arranged in an entry plane 21 which is arranged perpendicular to the hollow space axis 19. In the example shown, a second part of the margin lies in the base surface 13. In the embodiment in accordance with FIG. 1 b, the first part of the margin is made as an edge which results from the superimposition of the spherical section shown in broken lines and the hollow space 17. In the embodiment in accordance with FIG. 1a, the first part of the margin is rounded. Generally, the hollow space can also have a rotationally symmetrical shape differing from a conical stump, for example the shape of a spheroid or of an ellipsoid or of a cylinder. The implant shown in FIGS. 1 a and 1 b can, for example, be manufactured in that, starting from the planar base surface, a hollow space rotationally symmetrical around a hollow space axis is generated at an angle with respect to the polar axis in a fully spherical section having a spherical surface region, a planar base surface and a polar axis standing perpendicular to the planar base surface or the hollow space is generated with the hollow space axis in a full sphere or in a fully spherical section and a planar base surface is then manufactured perpendicular to the polar axis.

The embodiments shown in FIGS. 2a to 2i differ from one another by their conical opening angles 2δ and/or by the angles α respectively formed between the hollow space axis 19 and the polar axis 15 in order to be able to cover different varus/valgus positions and/or CCD angles which occur in practice. The embodiments in accordance with FIGS. 2a to 2c each have a conical opening angle of 2δ of 16°. The embodiments in accordance with FIGS. 2d to 2f each have a conical opening angle 2δ of 35°. The embodiments in accordance with FIGS. 2g to 2i each have a conical opening angle of 2δ of 50°. The embodiments in accordance with FIGS. 2a, 2d and 2g each have an angle α of 15°. The embodiments in accordance with FIGS. 2b, 2e and 2h each have an angle α of 25°. The embodiments in accordance with FIGS. 2c, 2f and 2i each have an angle α of 35°

FIG. 3a shows a side view of a femur 47 having a femoral head 49, a femoral neck 51 and a trochanter major 53, with an implant being implanted on the femoral head 49. Furthermore, the planar base surface 13' of the spherical section indicated in FIG. 1 is shown in broken lines. FIG. 3b shows a longitudinal section through the femur 47 and the implant of FIG. 3a. The external shape of the femoral stump 35 remaining after the preparation in accordance with FIG. 3b corresponds to the inner shape of the implant formed by the hollow space 17 or by the inner surface 23, 25. The hollow space 17 and the prepared femoral stump 35 form mating forms with one another. The implanted implant is thereby seated over the full area on the prepared femoral stump 35, with in particular a contact surface of conical stump shape between the femoral stump 35 and the implant making a conical seat possible as a primary anchorage and with a permanent compression strain acting on the bone with a corresponding choice of the conical angle so that a permanent bone stimulation is achieved. A bone degradation due to a lack of mechanical stimulation is thereby countered.

Figure 4:
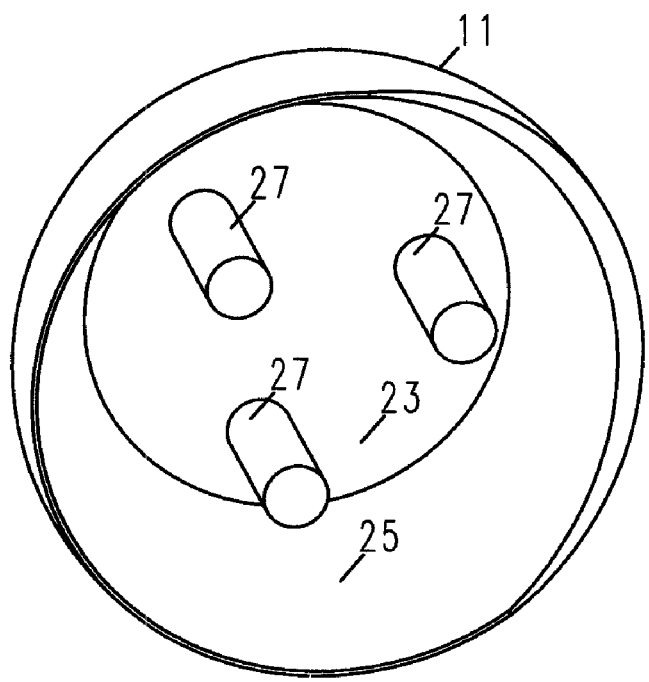
FIG. 4 shows a further embodiment of an implant with pin-like anchorage elements.
Figure 4:
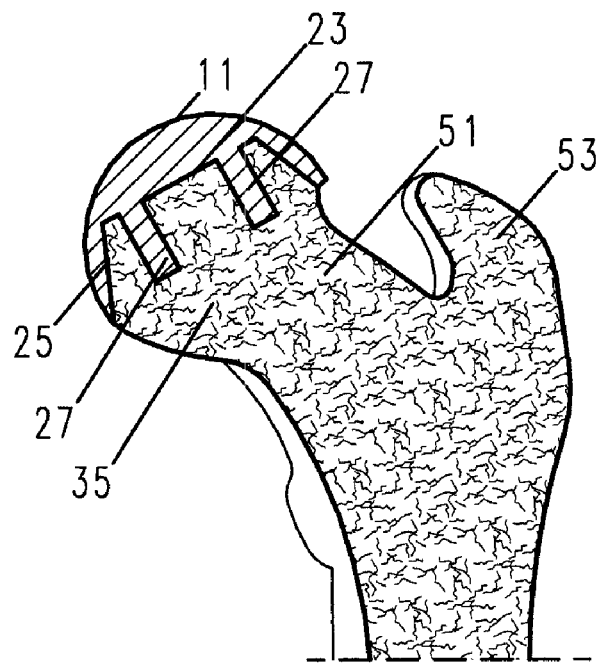

To strengthen the holding of the implant on the prepared stump 35, the implant is provided in accordance with a further embodiment shown in FIG. 4a with a plurality of anchorage pins 27 which are oriented parallel to the hollow space axis and which are attached to the end face 23 of the inner surface 23, 25 of the implant and project into the hollow space 17. The anchorage pins 27 are distributed symmetrically around the hollow space axis. The anchorage of the implant in accordance with this embodiment is shown in FIG. 4b.

Figure 5:
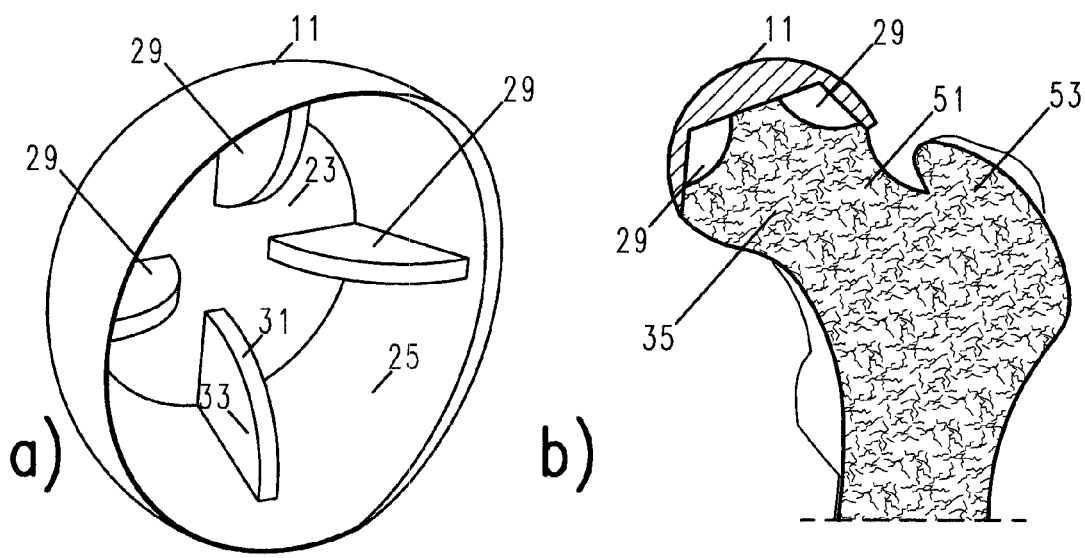
FIG. 5 shows another embodiment of an implant with fin-like anchorage elements.
Figure 5:
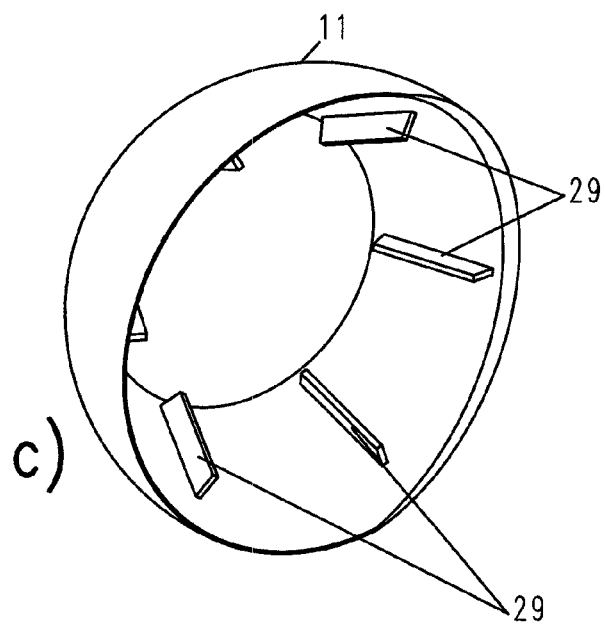

In another embodiment of the implant in FIG. 5a, anchorage fins 29 are provided as the anchorage elements and their flat sides 33 extend parallel to the hollow space axis and are likewise distributed symmetrically around the hollow space axis. The anchorage fins 29 adjoin both the end face 23 and the conical jacket surface 25 of the inner side 23, 25 of the implant. The inwardly facing marginal sides 31 of the fins 29 are each disposed on a circle around a center located outside the outer surface 13, 39 of the implant. The anchorage of the implant in accordance with this embodiment is shown in FIG. 5b. The slots required for the reception of the anchorage fins 29 in the prepared femoral head 35 can be manufactured simply by cutting or sawing in using a cutting instrument which is guided, for example, by means of a suitable gauge. A further exemplary embodiment of the implant with fins 29 arranged in the hollow space is shown in FIG. 5c.

Figure 6:
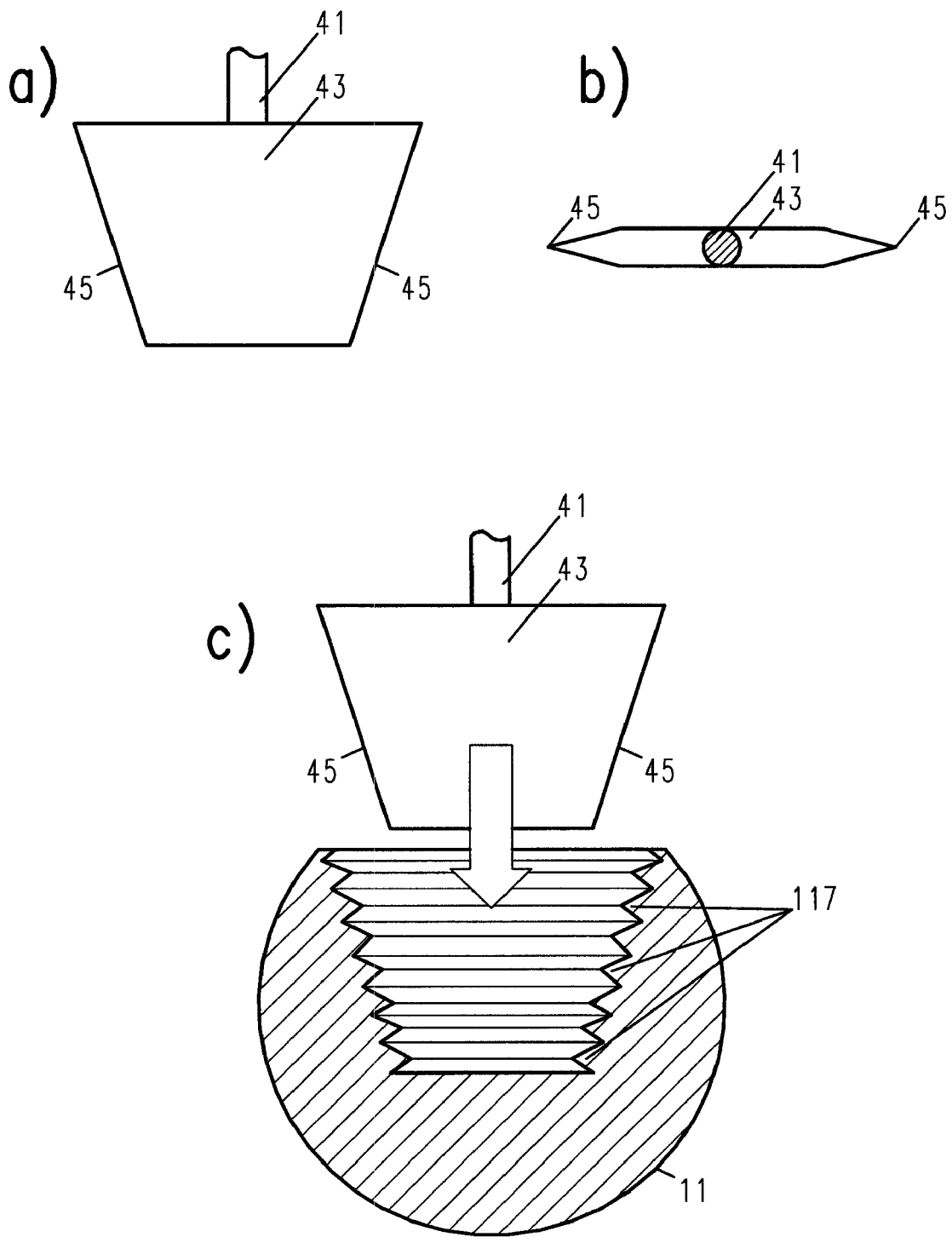
FIG. 6 shows an embodiment of a stamping instrument for the manufacture of toothed arrangements in the hollow space.

The end face or the jacket face or the total inner surface of an implant of the described kind is rough blasted, for example. The ingrowth of bone material into the implant is thereby promoted. For the better holding of the implant, the conical jacket surface can furthermore have barb-like structures such as have become known, for example, from EP 0639356, the entire disclosure of which is hereby incorporated by reference herein, said specification representing an integral part of this description in this respect, for use at the outer surface of a hip shell, for example a plurality of anchorage teeth which are arranged concentrically around the hollow space axis and are bent facing away from an opening of the hollow space into the interior of the implant. The barb-like structure can be manufactured, for example, in that peripheral grooves are first generated by turning on the inner surface of a hollow space 17 of a spherical section 11 symmetrical around a hollow space axis such that elevated portions 171 arise in the form of concentric rings between the grooves around the hollow space axis; this is shown schematically in FIG. 6c. Then, the instrument 43, which is shown in a side view in FIG. 6a and in a plan view in FIG. 6b, is introduced into the hollow space and pressed against the elevated portions while applying a force directed into the hollow space in the direction of the hollow space axis, as indicated by the arrow in FIG. 6c, to thereby notch the ring-shaped elevated portions by means of a stamping process so that a plurality of anchorage teeth arise from each ring-shaped elevated portion. In this process, the anchorage teeth are additionally plastically deformed at least in corner regions and are bent facing into the interior of the implant. It must be noted in this method that the originally generated hollow space has to be manufactured with a diameter undersize with respect to the desired dimension according to which the preparation of the stump is dimensioned since the hollow space is made even larger in its diameter by the grooves to be worked in. The embodiment shown in FIG. 6 of an instrument for the generation of the notches explained in the above has a shaft 41 for the gripping of the instrument and a head part 43 connected to the shaft 41. The head part 43 comprises two stamping edges 45 which are oppositely disposed with respect to the shaft 41 and which have contours in the side view of FIG. 6a or 6c which are a mating shape to the jacket surface of the hollow space 17. The instrument can also be made in the manner of star with a plurality of stamping edges distributed around the periphery, whereby a plurality of teeth can be manufactured along the periphery of the hollow space in one workstep.

The implant is present, for example, in the form of an implant kit with different diameters of the spherical articulation surface and/or different angles between the polar axis and the hollow space axis and/or different conical angles with which kit all the femoral head sizes, CCD angles and further indications can be covered which occur in practice. The spherical diameters of the spherical sections extend, for example, over the range from 38 mm to 60 mm.

The material used for the manufacture of the implant is not primarily essential to the invention; with the diameters of the articulation surface considered here, however, hard, wear-resistant materials such as metal or ceramic material in accordance with the prior art are used in practice for reasons of tribology. The implant is then used, for example, in conjunction with a suitable acetabular cup having an articulation surface made of a correspondingly wear-resistant material, that is, for example, as a metallic femoral component having an acetabular component with an articulation surface of metal or of highly cross-linked polyethylene or as a ceramic femoral component having an acetabular component with an articulation surface of a ceramic material of highly cross-linked polyethylene. In recent times, however, there have also already been endeavors to make the articulation surfaces of resurfacing implants from a soft, relatively yielding material which are provided to articulate with respect to an acetabular articulation surface with similar properties of hardness or "softness".

Figure 3:
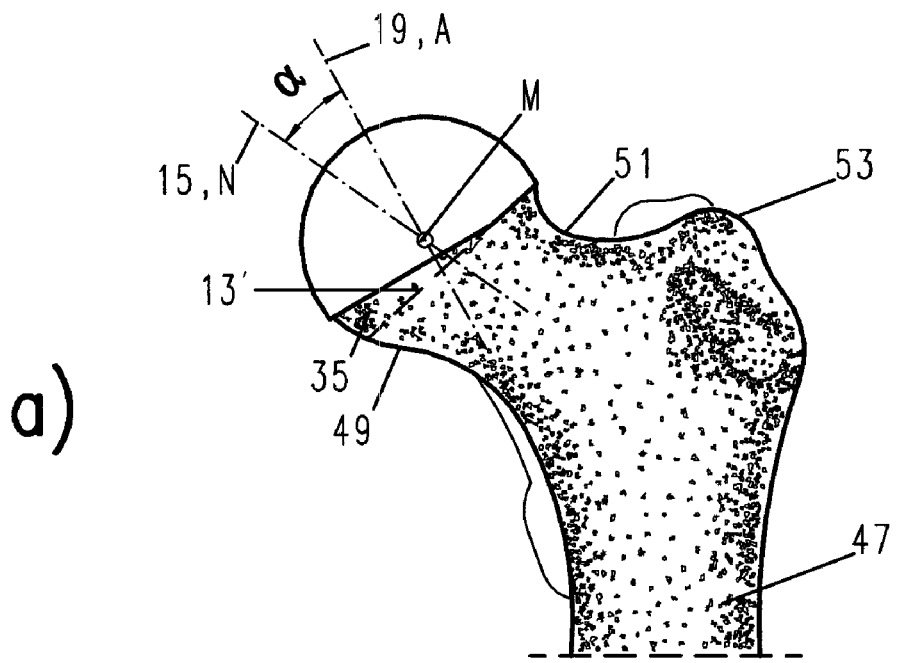
Figure 3:
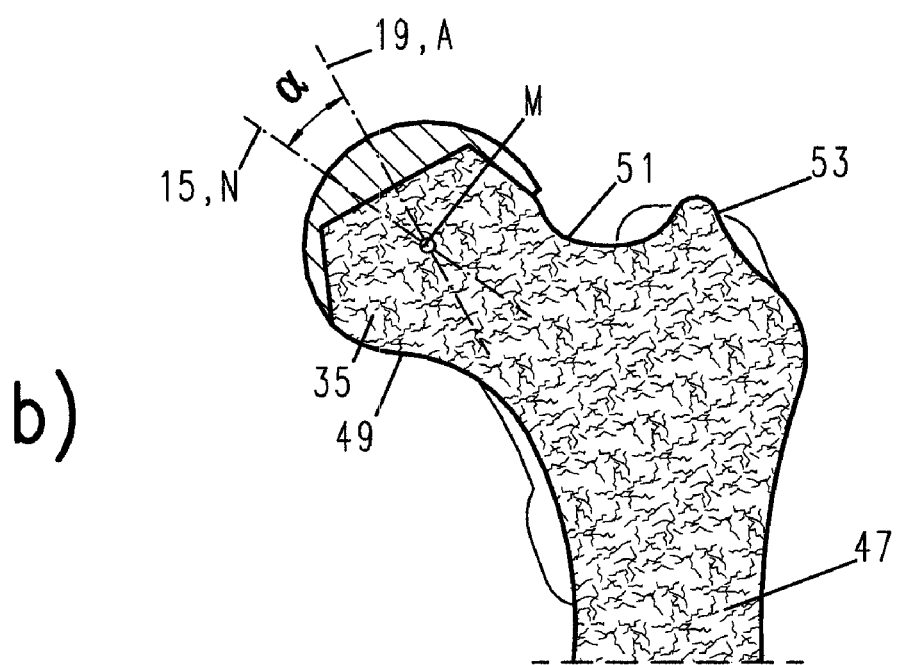
Figure 7:
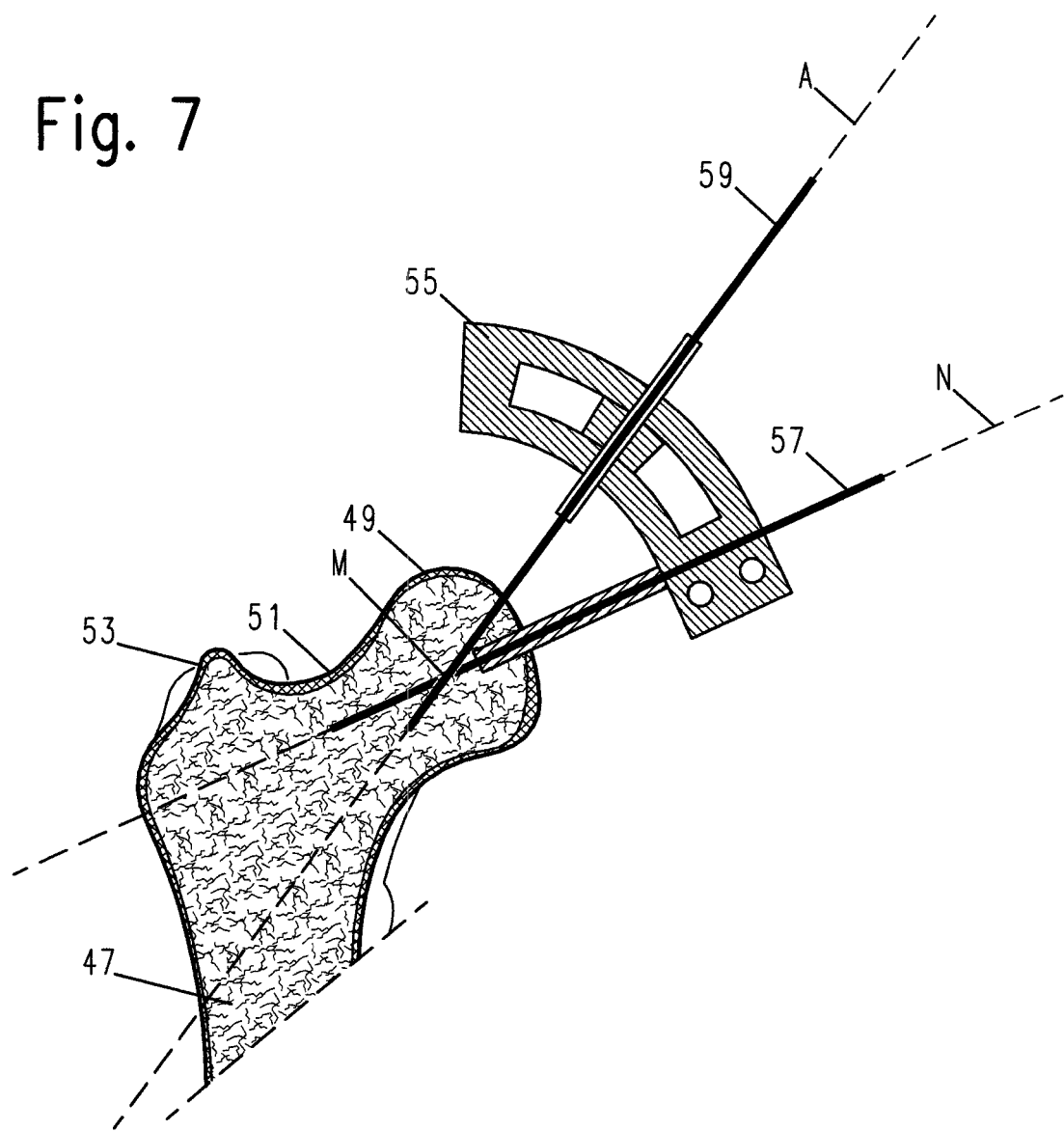
FIG. 7 shows an embodiment of an alignment instrument for the defining of an inclination of an implant axis to a femoral neck axis.

In an exemplary method for the implanting onto a femoral head of an implant made in cap shape and explained above, in accordance with FIG. 7, a first drill wire 57 is first inserted into the femoral head 49 along the femoral neck axis N. Subsequently, an implantation axis A for the implant is defined which corresponds at least substantially to the direction of the main strain on the femoral head 49. For this purpose, an alignment instrument 55 having an indication and/or gauge means is set onto the first drill wire 57 to define the inclination of the implantation axis A with respect to the femoral neck axis N, which inclination, for example, substantially corresponds to the angle between the hollow space axis and the polar axis of an implant explained above. In this context, for example, a suitable auxiliary means, for example a mechanical auxiliary means, is also used to localize the center M of the femoral head so that the center of the rotation between the neck axis and the implantation axis can be placed there. Subsequently, a second drill wire 59 is inserted into the femoral head 49 along the defined implantation axis A. Then the alignment instrument 55 and the first drill wire 57 are removed again. Subsequently, the second drill wire 59 is utilized as a guide tool for a suitable working instrument, for example a conical stump cutter, to work the femoral head 49 such that a prepared stump is formed therefrom which represents a mating shape to the hollow space of an implant described above and is rotationally symmetrical with respect to the implantation axis A. Subsequently, the second drill wire 59 is removed again. Then the implant, in particular an implant of the type described above, is guided to the prepared stump and placed on it such that the hollow space axis of the implant and the implantation axis coincide. The implant can be secured in this connection against tilting of the hollow space axis with respect to the implantation axis. An implant implanted in accordance with this method onto a prepared femoral head 35 is shown in FIG. 3. The implant is oriented on the prepared femoral head 35 such that the polar axis 15 of the implant coincides with the neck axis N of the prepared femoral head 35 and the hollow space axis 19 of the implant coincides with the implantation axis A which corresponds to the main strain direction of the femoral head or at least coincide to a good approximation in practice. In FIG. 3, the implantation axis A is only inclined in a frontal axis with respect to the femoral neck axis N. Generally, however, the implantation axis A can also additionally be inclined in a sagittal plane with respect to the femoral neck axis N; this is termed antetorsion.

In view of the statements made here, further embodiments of the invention characterized in the claim become clear to the person skilled in the art which cannot be shown conclusively here.

What is claimed is:

1. A method for implantation of an implant made in a cap shape onto a femoral head of a femur, comprising:
    choosing an implant made in a cap shape which comprises:
        a spherical outer surface defining a polar axis extending through a spherical center (M),
        a planar base, said polar axis perpendicular to a plane containing said planar base;
        a hollow space which is rotationally symmetrical about a hollow space axis the hollow space axis forming an angle α different than zero to the polar axis;
    resecting the femoral head so as to obtain a prepared stump representing a mating shape to the hollow space of the implant and being rotationally symmetrical with respect to an implantation axis (A); and
    working the femoral head so that the implantation axis (A) is inclined at least in a frontal plane with respect to the femoral neck axis (N) of the femur.

2. A method in accordance with claim 1, further comprising:
    inserting a first drill wire into the femoral head along the femoral neck axis (N),
    placing an alignment instrument onto the first drill wire, said alignment instrument comprising an indication means for defining the inclination of the implantation axis (A) with respect to the femoral neck axis (N) and thus defining the implantation axis (A);
    inserting a second drill wire into the femoral head along the implantation axis (A) inclined with respect to the femoral neck axis (N); and
    removing the alignment instrument and the first drill wire before the resecting of the femoral head.

3. A method in accordance with claim 2, further comprising using the second drill wire as a guide tool in the working of the femoral head.

4. A method in accordance with claim 2, further comprising removing the second drill wire before placing the implant made in cap shape onto the prepared stump.

5. A method in accordance with claim 2, further comprising implanting the implant such that the hollow space axis and the implantation axis (A) coincide on the placing of the implant made in cap shape onto the prepared stump.

6. A method in accordance with claim 5, further comprising securing the implant against tilting of the hollow space axis with respect to the implantation axis (A).

7. A method in accordance with claim 2, further comprising working the femoral head so that the implantation axis (A) is inclined with respect to the femoral neck axis (N) both in the frontal plane and in a sagittal plane.

8. A method in accordance with claim 1, wherein the step of working the femoral head such that the inclination of the implantation axis (A) with respect to the femoral neck axis (N) corresponds to the angle between the polar axis and the hollow space axis of the implant.

9. A method in accordance with claim 1, further comprising placing the implant on the prepared stump of the femoral head such that the polar axis of the implant and the femoral neck axis (N) coincide.

10. A method in accordance with claim 1, wherein the angle α lies in the range of 15° to 50°.

* * * * *

UNITED STATES PATENT AND TRADEMARK OFFICE
CERTIFICATE OF CORRECTION

PATENT NO. : 8,394,149 B2
APPLICATION NO. : 12/858556
DATED : March 12, 2013
INVENTOR(S) : Howald et al.

It is certified that error appears in the above-identified patent and that said Letters Patent is hereby corrected as shown below:

On the title page, in column 2, under Item (56) "Other Publications", line 1, after "Arthropometry"", insert --,--, therefor On the title page, in column 2, under Item (57) "Abstract", line 2, delete "(a)" and insert --($\alpha$)--, therefor On title page 3, in column 1, under Item (56) "Foreign Patent Documents", line 6, delete "W0" and insert --WO--, therefor On title page 3, in column 1, under Item (56) "Foreign Patent Documents", line 7, delete "W0" and insert --WO--, therefor On title page 3, in column 1, under Item (56) "Foreign Patent Documents", line 8, delete "W0" and insert --WO--, therefor On title page 3, in column 1, under Item (56) "Foreign Patent Documents", line 9, delete "W0" and insert --WO--, therefor On title page 3, in column 2, under Item (56) "Other Publications", line 1, delete "J.S." and insert --J. S.--, therefor On title page 3, in column 2, under Item (56) "Other Publications", line 1, delete "P.C." and insert --P. C.--, therefor Signed and Sealed this
Fourth Day of February, 2014

Michelle K. Lee
*Deputy Director of the United States Patent and Trademark Office*